(12) United States Patent
Niwa et al.

(10) Patent No.: US 10,087,469 B2
(45) Date of Patent: Oct. 2, 2018

(54) METHOD OF PRODUCING SUGAR SOLUTION, SUGAR SOLUTION, AND METHOD OF PRODUCING ETHANOL

(71) Applicant: Toray Industries, Inc., Tokyo (JP)

(72) Inventors: Masahiro Niwa, Tokyo (JP); Sho Shindo, Akita (JP); Takanori Nishida, Akita (JP); Junpei Kishimoto, Kanagawa (JP); Atsushi Minamino, Kanagawa (JP); Hiroyuki Kurihara, Kanagawa (JP); Katsushige Yamada, Kanagawa (JP)

(73) Assignee: Toray Industries, Inc. (JP)

( * ) Notice: Subject to any disclaimer, the term of this patent is extended or adjusted under 35 U.S.C. 154(b) by 154 days.

(21) Appl. No.: 14/377,918

(22) PCT Filed: Feb. 12, 2013

(86) PCT No.: PCT/JP2013/053267
§ 371 (c)(1),
(2) Date: Aug. 11, 2014

(87) PCT Pub. No.: WO2013/122051
PCT Pub. Date: Aug. 22, 2013

(65) Prior Publication Data
US 2015/0004647 A1 Jan. 1, 2015

(30) Foreign Application Priority Data
Feb. 13, 2012 (JP) ................................. 2012-028962

(51) Int. Cl.
| | | |
|---|---|---|
| *C12P 7/10* | (2006.01) | |
| *C13K 1/02* | (2006.01) | |
| *C13K 13/00* | (2006.01) | |
| *C12P 19/02* | (2006.01) | |
| *C12P 19/14* | (2006.01) | |
| *C13K 1/04* | (2006.01) | |

(52) U.S. Cl.
CPC ................. *C12P 7/10* (2013.01); *C12P 19/02* (2013.01); *C12P 19/14* (2013.01); *C13K 1/02* (2013.01); *C13K 1/04* (2013.01); *C13K 13/002* (2013.01); *C12P 2201/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 8,497,091 B2 | 7/2013 | Hanakawa et al. |
| 8,765,405 B2 | 7/2014 | Kurihara et al. |
| 2013/0004994 A1 | 1/2013 | Hanakawa et al. |
| 2013/0092157 A1 | 4/2013 | Hanakawa et al. |
| 2013/0273608 A1 | 10/2013 | Hanakawa et al. |
| 2013/0312738 A1 | 11/2013 | Kishimoto et al. |

FOREIGN PATENT DOCUMENTS

| | | |
|---|---|---|
| JP | 62-201606 A | 9/1987 |
| JP | 2008-161125 A | 7/2008 |
| JP | 2009-296983 A | 12/2009 |
| WO | 2009/110374 A1 | 9/2009 |
| WO | 2010/067785 A1 | 6/2010 |
| WO | 2011/111451 A1 | 9/2011 |
| WO | 2011/162009 A1 | 12/2011 |
| WO | 2012/111794 | 8/2012 |

OTHER PUBLICATIONS

Michael J. Bowman et al., "Liquid chromatography-mass spectrometry investigation of enzyme-resistant xylooligosaccharide structures of switchgrass associated with ammonia pretreatment, enzymatic saccharification, and fermentation," Bioresource Technology, vol. 110, Jan. 28, 2012, pp. 437-447.

Extended European Search Report dated Jun. 12, 2015 from corresponding European Patent Application No. 13 748 499.4.

Nishioka, T. et al., "Isolation and Activity of N-p-Coumaroyltyramine, an α-Glucosidase Inhibitor in Welsh Onion (*Allium fistulosum*)," *Biosci. Biotech. Biochem.*, 1997, vol. 61, No. 7, pp. 1138-1141.

*Primary Examiner* — Jennifer M. H. Tichy
(74) *Attorney, Agent, or Firm* — DLA Piper LLP (US)

(57) ABSTRACT

A method of producing a sugar solution includes a pretreatment step of treating cellulosic biomass with a treatment agent containing ammonia to obtain an ammonia-treated product, an ammonia-treated sugar solution preparation step of enzymatically saccharifying the ammonia-treated product to obtain an ammonia-treated sugar solution, and a purified sugar solution preparation step of removing coumaramide and/or ferulamide in the ammonia-treated sugar solution by purification to obtain a purified sugar solution having a concentration of coumaramide and/or ferulamide of 10 to 1,100 ppm.

3 Claims, 6 Drawing Sheets

[PEAK OF AMMONIA-TREATED SUGAR SOLUTION 1]

FIG.4

[PEAK OF AMMONIA-TREATED SUGAR SOLUTION 2]

METHOD OF PRODUCING SUGAR SOLUTION, SUGAR SOLUTION, AND METHOD OF PRODUCING ETHANOL

TECHNICAL FIELD

This disclosure relates to a method of producing a sugar solution from cellulosic biomass, the sugar solution, and a method of producing ethanol.

BACKGROUND

A fermentation production process of a chemical substance from sugar as a raw material has been used in production of various industrial raw materials. Recently, as sugar used as a fermentation raw material, a substance derived from an edible raw material such as sugarcane, starch, and sugar beets has been industrially used. However, the edible raw material may be insufficient due to an increase in the global population in the future, and this may cause a sudden rise in prices. Therefore, development of a process to efficiently produce a sugar solution from a renewable inedible material, that is, cellulosic biomass has become an issue.

Cellulosic biomass mainly includes lignin that is an aromatic polymer, and cellulose and hemicellulose that each are a monosaccharide polymer. Examples of a method of producing a sugar solution from cellulosic biomass as a raw material may include a method of directly hydrolyzing cellulosic biomass as a raw material using concentrated sulfuric acid or the like, and a pretreatment-enzymatic saccharification method in which cellulosic biomass is subjected to a pretreatment such as a steam treatment, a fine pulverization treatment, and a treatment with dilute sulfuric acid in advance, to separate cellulose and hemicellulose from lignin, and cellulose and hemicellulose are hydrolyzed with a diastatic enzyme such as cellulase.

A sugar solution produced from cellulosic biomass obtained by these methods has a problem in which during a process of producing the sugar solution, a fermentation inhibitor such as hydroxymethyl furfural (HMF), furfural, and vanillin is produced and, during production of alcohol and the like by fermentation of the obtained sugar solution, fermentation of the sugar solution is inhibited. Further, the sugar concentration of a sugar solution to be obtained may be low depending on treatment conditions of production of the sugar solution. In that case, the sugar solution needs to be concentrated several times to about 10 times before the fermentation step. As a method of removing the fermentation inhibitor in the sugar solution and at the same time, increasing the sugar concentration during production of the sugar solution from the cellulosic biomass as the raw material, a method of treating the sugar solution using a nano-filtration membrane has been disclosed (for example, see International Publication Nos. 2009/110374 and 2010/067785).

In general, the pretreatment-enzymatic saccharification method has such an advantage that the environmental impact is smaller as compared with the method of directly hydrolyzing the raw material, but on the other hand, the sugar yield is low. As a pretreatment method in which the environmental impact is small and high sugar yield is obtained, a pretreatment method using a treatment agent containing ammonia has been proposed (for example, see Japanese Laid-open Patent Publication No. 2008-161125).

In general, in a sugar solution obtained from cellulosic biomass subjected to a pretreatment such as a steam treatment, as described above, a fermentation inhibitor such as hydroxymethyl furfural (HMF), furfural, and vanillin is produced during a process of producing the sugar solution, and fermentation of the sugar solution is inhibited during production of alcohol and the like by fermentation of the obtained sugar solution.

On the other hand, in a sugar solution obtained by the pretreatment-enzymatic saccharification method using the pretreatment with a treatment agent containing ammonia as described in JP '125, the above-described known fermentation inhibitor is hardly detected, but it is found that fermentation of the sugar solution is inhibited like a sugar solution obtained using cellulosic biomass.

Therefore, it could be helpful to provide a method of producing a sugar solution capable of improving the fermentation efficiency of the sugar solution during fermentation of the sugar solution obtained using cellulosic biomass pretreated with a treatment agent containing ammonia that can achieve high sugar yield to aim at improving the production efficiency of ethanol and the like using the sugar solution obtained from cellulosic biomass, as well as to provide a sugar solution and a method of producing ethanol.

SUMMARY

We discovered that a hydrolysate (ammonia-treated sugar solution) obtained by hydrolyzing, with an enzyme, cellulosic biomass pretreated with ammonia includes coumaramide and ferulamide as specific fermentation inhibitors. We also found that when coumaramide and/or ferulamide in the ammonia-treated sugar solution are removed by purification to set the concentration of coumaramide and/or ferulamide to a predetermined range, the fermentation efficiency of the ammonia-treated sugar solution can be improved.

We thus provide:

(1) A method of producing a sugar solution, including:
   a pretreatment step of treating cellulosic biomass with a treatment agent containing ammonia to obtain an ammonia-treated product;
   an ammonia-treated sugar solution preparation step of enzymatically saccharifying the ammonia-treated product to obtain an ammonia-treated sugar solution; and
   a purified sugar solution preparation step of removing coumaramide and/or ferulamide in the ammonia-treated sugar solution by purification to obtain a purified sugar solution having a concentration of coumaramide and/or ferulamide of 10 to 1,100 ppm.

(2) The method of producing a sugar solution according to the above-described (1), wherein the cellulosic biomass contains herbaceous biomass.

(3) The method of producing a sugar solution according to the above-described (1) or (2), wherein in a purification treatment of the ammonia-treated sugar solution, a nano-filtration membrane is used.

(4) The method of producing a sugar solution according to any one of the above-described (1) to (3), wherein the ammonia-treated product is enzymatically saccharified with a solution having a concentration of a solid matter of the ammonia-treated product within a range of 1 to 10% by mass during enzymatic saccharification of the ammonia-treated product.

(5) A sugar solution obtained by the method of producing a sugar solution according to any one of the above-described (1) to (4).

(6) A method of producing ethanol using the sugar solution according to the above-described (5) as a fermentation raw material.

When a sugar solution obtained using cellulosic biomass pretreated with a treatment agent containing ammonia is fermented, the fermentation efficiency of the sugar solution can be improved.

DETAILED DESCRIPTION

Hereinafter, examples of our methods and solutions will be described in detail with reference to the drawings. This disclosure is not limited to the examples. In addition, constituents in the following examples include those that can be easily assumed by those skilled in the art, those that are substantially equivalent, and so-called "equivalents." Further, the constituents may be used in appropriate combination or by appropriate selection.

Figure 1:
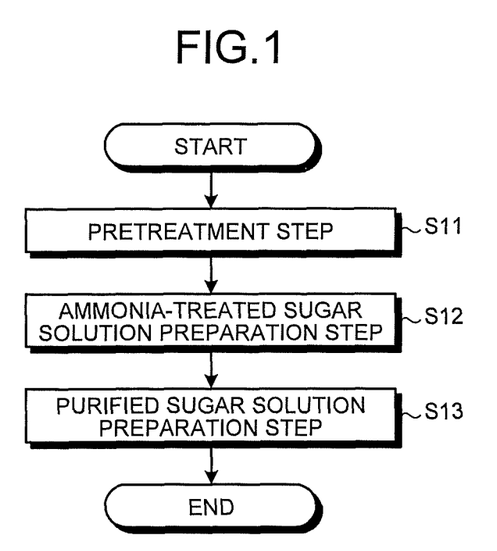
FIG. 1 is a flow chart showing an example of a method of producing a sugar solution according to an example.

The method of producing a sugar solution will be described with reference to the drawings. FIG. 1 is a flow chart showing an example of the method of producing a sugar solution. As shown in FIG. 1, the method of producing a sugar solution includes the following steps:

(A) a pretreatment step of treating cellulosic biomass with a treatment agent containing ammonia to obtain an ammonia-treated product (step S11);

(B) an ammonia-treated sugar solution preparation step of enzymatically saccharifying the ammonia-treated product to prepare an ammonia-treated sugar solution (step S12); and (C) a purified sugar solution preparation step of removing coumaramide and/or ferulamide in the ammonia-treated sugar solution by purification to obtain a purified sugar solution having a concentration of coumaramide and/or ferulamide of 10 to 1,100 ppm (step S13).

Cellulosic biomass means herbaceous biomass such as bagasse, switch grass, napier-grass, erianthus, corn stover (corn stem), rice straw, and barley straw, or woody biomass such as tree and waste building materials. The cellulosic biomass contains polysaccharide such as cellulose and hemicellulose. A sugar solution can be produced by hydrolysis of such polysaccharide.

In general, hydrolysis of cellulosic biomass is referred to as saccharification. In this example, a sugar solution produced by saccharification of cellulosic biomass is referred to as a cellulose-derived sugar solution. The cellulose-derived sugar solution includes monosaccharide such as glucose, xylose, mannose, and arabinose, and water-soluble polysaccharide such as cellobiose, cellooligosaccharide, and xylooligosaccharide. Such saccharides can be used as a fermentation raw material (carbon source) of a microorganism, and converted by the microorganism into various chemical substances such as ethanol, lactic acid, and amino acid.

Pretreatment Step: Step S11

Cellulosic biomass is treated with a treatment agent containing ammonia to obtain an ammonia-treated product (pretreatment step: step S11). In general, examples of a method of pretreating cellulosic biomass may include a steam treatment, a fine pulverization treatment, a blasting treatment, an acid treatment with an acidic solution of sulfuric acid or the like, an alkali treatment with an alkaline solution of sodium hydroxide or the like, a treatment with ammonia ($NH_3$), an enzymatic treatment, and a treatment with a compound containing an amino group ($NH_2$). Among these pretreatment methods, according to this example, cellulosic biomass is pretreated with a treatment agent containing ammonia. Ammonia is easily obtained and handled. By a pretreatment method with a treatment agent containing ammonia, cellulosic biomass can be effectively saccharified as compared with other pretreatment methods. When cellulosic biomass is pretreated with a treatment agent containing ammonia in advance before saccharification, the saccharification efficiency of the cellulosic biomass can be improved.

As the treatment agent containing ammonia, ammonia may be used in combination with some of a compound containing an amino group and another compound. Examples of the compound containing an amino group may include methylamine, ethylamine, propylamine, butylamine, hydrazine, ethylenediamine, propanediamine, and butanediamine. Examples of the other compound may include carbon dioxide, nitrogen, ethylene, methane, ethane, propane, butane, pentane, hexane, toluene, benzene, phenol, dioxane, xylene, acetone, chloroform, carbon tetrachloride, ethanol, methanol, propanol, and butanol.

In this example, the treatment agent containing ammonia may be any of a liquid, a gas, and a gas-liquid mixed phase. Even when ammonia is used in any state of a liquid, a gas, and a gas-liquid mixed phase, cellulosic biomass having excellent enzymatic saccharification efficiency can be obtained. The treatment agent containing ammonia may be a supercritical ammonia fluid or a subcritical ammonia fluid. A treatment method with a supercritical ammonia fluid is not particularly limited, and may be appropriately selected depending on a purpose. For example, this treatment method can be performed by introducing cellulosic biomass and ammonia into a reactor such as an autoclave, and applying heat and pressure to the inside of the reactor to make ammonia into a supercritical state. Since the supercritical ammonia fluid has high permeability into the inside of cellulosic biomass, cellulosic biomass suitable for enzymatic saccharification can be obtained efficiently and quickly.

In this example, gathered cellulosic biomass may be used as it is, or cellulosic biomass may be cut or pulverized in advance before a pretreatment, to form cellulosic biomass particles having an average particle diameter that is equal to or less than a predetermined particle diameter, and then pretreated. When the particle diameter of cellulosic biomass is decreased in advance, handling is easy and the efficiency of treatment with the treatment agent containing ammonia can be improved.

The particle diameter of particles of cellulosic biomass is not particularly limited, and may be appropriately selected depending on the purposes thereof. For example, the particle diameter is preferably 5 mm or smaller, more preferably 1 mm or smaller, and further preferably 0.1 mm or smaller. When the particle diameter of particles of cellulosic biomass is greater than 5 mm, the cellulosic biomass may not be sufficiently subjected to a saccharification treatment. When the particle diameter of particles of cellulosic biomass falls within the above-described range, a time required for the saccharification treatment of the cellulosic biomass can be shortened and the amount of ammonia to be used can be decreased.

In this example, gathered cellulosic biomass may be used as it is and pretreated with the treatment agent containing ammonia, but this disclosure is not limited to this. From the viewpoint of recovery of ammonia to be used in a pretreatment of cellulosic biomass, the cellulosic biomass may be dried and pretreated by addition of the treatment agent containing ammonia.

In this example, as the method of pretreating cellulosic biomass, a treatment method with the treatment agent containing ammonia is used, but the treatment method with the treatment agent containing ammonia may be used in combination with the other method of pretreating cellulosic biomass as described above.

Ammonia-Treated Sugar Solution Preparation Step: Step S12

An enzyme is added to the ammonia-treated product obtained in the pretreatment step (step S11), to perform saccharification by an enzymatic treatment, and an ammonia-treated sugar solution (hydrolysate) is obtained (ammonia-treated sugar solution preparation step: step S12). In this example, the sugar solution obtained by saccharification of the cellulosic biomass treated with the treatment agent containing ammonia is referred to as an ammonia-treated sugar solution.

The sugar solution prepared from cellulosic biomass (cellulose-derived sugar solution) contains a fermentation inhibitor(s), of which the amount or component varies depending on a pretreatment or saccharification method. Fermentation inhibition means a phenomenon in which when a chemical substance is produced as a fermentation raw material from the cellulose-derived sugar solution, the growth rate of a microorganism, the production amount, cumulative dose, and production rate of the chemical substance decrease as compared with use of a sample monosaccharide as the fermentation raw material. The fermentation inhibitor represents a causative substance of causing a fermentation inhibition phenomenon in such a fermentation step to prevent a fermentation reaction. Specific examples of the fermentation inhibitor may include acetic acid, formic acid, levulinic acid, furfural, and hydroxymethyl furfural (HMF) which are excessively decomposed substances of sugar, and vanillin, acetovanillin, and guaiacol which are aromatic compounds derived from lignin.

The ammonia-treated sugar solution contains coumaramide and ferulamide as the fermentation inhibitors. Coumaramide and ferulamide are not contained in a cellulose-derived sugar solution obtained by a treatment other than the treatment with ammonia, but are contained in the ammonia-treated sugar solution. Therefore, coumaramide and ferulamide are specific fermentation inhibitors contained in the ammonia-treated sugar solution. Coumaramide and ferulamide are amide compounds produced by condensation of coumaric acid and ferulic acid with ammonia, respectively. Coumaric acid or ferulic acid is contained in cellulosic biomass. Therefore, coumaramide and ferulamide in the ammonia-treated sugar solution are produced by condensation reactions of coumaric acid and ferulic acid, respectively, in cellulosic biomass with an ammonia molecule by the treatment with ammonia during addition of the treatment agent containing ammonia to the cellulosic biomass in the pretreatment step (step S11).

Even when herbaceous or woody cellulosic biomass is used as the raw material, coumaramide and ferulamide are contained in the ammonia-treated sugar solution. However, when the herbaceous biomass is used as the raw material, coumaramide and ferulamide are contained in larger amounts. Therefore, when the ammonia-treated sugar solution is used as the fermentation raw material as it is without purification, the fermentation efficiency when the herbaceous biomass is used as the raw material is lower than that when the woody biomass is used as the raw material. However, even when the herbaceous or woody biomass is used as the raw material, the same fermentation efficiency can be obtained by purification of the ammonia-treated sugar solution. The reason why the amounts of coumaramide and ferulamide in the ammonia-treated sugar solution when the herbaceous biomass is used as the raw material are larger than those when the woody biomass is used as the raw material is because the amounts of coumaric acid and ferulic acid in the herbaceous biomass are originally larger than those in the woody biomass.

It is preferable that the ammonia-treated product be enzymatically saccharified with a solution having a concentration of solid matters of the ammonia-treated product within a range of 1% by mass or more and 10% by mass or less during enzymatic saccharification of the ammonia-treated product. The concentration of solid matters of the ammonia-treated product is more 5% by mass or more and less than 10% by mass. When the concentration of solid matters of the ammonia-treated product is 10% by mass or less, a saccharification reaction is not inhibited during enzymatic saccharification of the ammonia-treated product by addition of an enzyme to the ammonia-treated product in the ammonia-treated sugar solution preparation step as described below (step S12). Further, an increase in the concentration of the fermentation inhibitor in the ammonia-treated sugar solution can be suppressed. When the concentration of solid matters of the ammonia-treated product is 1% by mass or more, energy and treatment time can be suppressed during concentrating to a concentration required for use as a raw material for fermentation production, and the cost can be decreased. Therefore, this is economically advantageous.

A solvent component containing the solid matters of the ammonia-treated product is not limited as long as the solid matters of the ammonia-treated product can be dispersed therein. Water or the like is used.

The enzyme used for enzymatic saccharification of the ammonia-treated product is not particularly limited as long as it is an enzyme having a cellulose decomposition activity (cellulase). As the enzyme, cellulase containing exo-type cellulase or endo-type cellulase that has a crystalline cellulose decomposition activity is preferably used. It is preferable that such cellulase be cellulase produced by filamentous fungi, more preferably cellulase produced by *Trichoderma* spp., among filamentous fungi, and further preferably cellulase produced by *Trichoderma reesei* among *Trichoderma* spp.

The enzymatic saccharification is performed preferably at a pH of about 3 to about 7, and more preferably about 5. Further, the reaction temperature of the enzymatic saccharification is preferably 40 to 70° C., and more preferably about 50° C.

The ammonia-treated sugar solution obtained by the enzymatic saccharification may be subjected to a subsequent step as it is, or after removal of solid matters by solid-liquid separation such as a centrifugal separation method and a membrane separation method.

Purified Sugar Solution Preparation Step: Step S13

Coumaramide and/or ferulamide contained in the ammonia-treated sugar solution obtained in the ammonia-treated sugar solution preparation step (step S12) are removed by purification to obtain a purified sugar solution having a predetermined concentration (purified sugar solution preparation step: step S13).

The concentration of coumaramide and/or ferulamide in the purified sugar solution is 10 to 1,100 ppm, more preferably 10 to 800 ppm, and further preferably 10 to 450 ppm. When the concentration of coumaramide and/or ferulamide in the purified sugar solution is 1,100 ppm or less, the fermentation efficiency is significantly improved. When the concentration in the purified sugar solution is 10 ppm or more, an increase in energy and cost required for purification of the ammonia-treated sugar solution can be suppressed. In other words, although the fermentation efficiency of the purified sugar solution is more improved as the concentration of coumaramide and/or ferulamide is lower, when the concentration in the purified sugar solution is less than 10 ppm, the fermentation efficiency of the purified sugar solution is not further improved and energy and cost required for purification of the ammonia-treated sugar solution only increases. Therefore, this is economically disadvantageous, and is not preferable.

A method of purifying the ammonia-treated sugar solution is not particularly limited, and examples thereof may include distillation, extraction, crystallization, recrystallization, column chromatography, and membrane separation. These methods of purifying the ammonia-treated sugar solution may be used alone or a plurality of the methods may be used in combination. Among the methods of purifying the ammonia-treated sugar solution, a membrane treatment is preferably used, and in particular, a nano-filtration membrane is preferably used. The nano-filtration membrane is able to prevent permeation of sugar in the ammonia-treated sugar solution and allows coumaramide and/or ferulamide to permeate. Therefore, use of the nano-filtration membrane in purification of the ammonia-treated sugar solution enables both sugar concentration and removal of ferulamide and coumaramide.

The nano-filtration membrane is a separation membrane generally defined as "membrane that allows monovalent ions to permeate and prevents divalent ions," and is also referred to as a nano-filter, a nano-filtration membrane, or an NF membrane. The nano-filtration membrane is a membrane that may have fine void spaces of some nanometers, and is mainly used for prevention of fine particles, molecules, ions, salts, and the like, in water.

As a material to form the nano-filtration membrane, a macromolecular material such as cellulose acetate-based polymer, polyamide, polyester, polyimide, and vinyl polymer can be used. The nano-filtration membrane is not limited to a film made of one kind of the foregoing materials, and a membrane containing a plurality of membrane materials may be used. The membrane structure of the nano-filtration membrane may be an asymmetric membrane that has a compact layer on at least one side and micropores of which the diameter gradually increases from the compact layer toward the inside of the membrane or toward another side or a composite membrane having a very thin functional layer made of another material on the compact layer of the asymmetric membrane. As the composite membrane, for example, a composite membrane constituting a nano-filter that has a polyamide functional layer on a support membrane made of polysulfone as a membrane material can be used. For example, such a composite membrane is described in Japanese Patent Application Laid-Open No. Sho. 62-201606.

In particular, a composite membrane that has high pressure resistance, high water permeability, and high solute removal performance, and excellent potential, and includes a functional layer of polyamide is preferable. To maintain durability against operation pressure, high water permeability, and prevention performance, a membrane having a structure in which a functional layer is polyamide and is held by a porous membrane or a support made of non-woven fabrics is suitable. It is suitable that a polyamide semipermeable membrane be a composite semipermeable membrane having a functional layer of crosslinked polyamide obtained by a polycondensation reaction of a polyfunctional amine with a polyfunctional acid halide on a support.

Examples of preferred carboxylic acid component that is a monomer constituting polyamide in the nano-filtration membrane having a functional layer of polyamide may include an aromatic carboxylic acid such as trimesic acid, benzophenone tetracarboxylic acid, trimellitic acid, pyromellitic acid, isophthalic acid, terephthalic acid, naphthalenedicarboxylic acid, diphenylcarboxylic acid, and pyridine carboxylic acid. In consideration of solubility of a solvent to form a membrane, trimesic acid, isophthalic acid, terephthalic acid, and a mixture thereof are more preferable.

Examples of preferred amine component that is a monomer constituting polyamide may include primary diamine having an aromatic ring such as m-phenylenediamine, p-phenylenediamine, benzidine, methylenebisdianiline, 4,4'-diaminobiphenyl ether, dianisidine, 3,3',4-tri-aminobiphenyl ether, 3,3',4,4'-tetraminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-aminobenzoyl)-p(m)-phenylenediamine-2,2'-bis (4-aminophenylbenzimidazole), 2,2'-bis(4-aminophenyl-benzoxazole), and 2,2'-bis(4-aminophenylbenzothiazole), and secondary diamine such as piperazine, piperidine, and derivatives thereof. In particular, a nano-filtration membrane having a functional layer of crosslinked polyamide containing piperazine or piperidine as the monomer is preferably used since it has heat resistance and chemical resistance in addition to pressure resistance and durability. Polyamide that contains crosslinked piperazine polyamide or crosslinked piperidine polyamide as a main component and a component represented by Formula (1) is more preferable, and polyamide that contains crosslinked piperazine polyamide as a main component and the component represented by Formula (1) is further preferable. The component represented by Formula (1) wherein n is 3 is preferably used. Examples of a nano-filtration membrane having a functional layer of polyamide that contains crosslinked piperazine polyamide as a main component and the component represented by Formula (1) may include those described in Japanese Patent Application Laid-Open No. Sho. 62-201606. Specific examples thereof may include a crosslinked piperazine polyamide-based nano-filtration membrane UTC60 available from TORAY INDUSTRIES, INC., which has a functional layer of polyamide that contains crosslinked piperazine polyamide as a main component and the component represented by Formula (1), wherein n is 3:

(1)

(n is an integer 1 or more).

The nano-filtration membrane is generally used as a spiral membrane module. The nano-filtration membrane used in this example is preferably used as a spiral membrane module. Specific examples of preferred nano-filtration membrane module may include a nano-filtration membrane GEsepa available from GE Osmonics, Inc., which is a cellulose acetate-based nano-filtration membrane, a nano-filtration membrane NF99 or NF99HF available from Alfa Laval, which has a functional layer of polyamide, a nano-filtration membrane NF-45, NF-90, NF-200, NF-270, or NF-400 available from Filmtech corporation, which has a functional layer of crosslinked piperazine polyamide, and a nano-filtration membrane module SU-210, SU-220, SU-600, or SU-610 available from TORAY INDUSTRIES, INC., including UTC60 available from TORAY INDUSTRIES, INC., which has a functional layer that contains crosslinked piperazine polyamide as a main component and a polyamide containing a component represented by Formula (1). A nano-filtration membrane NF99 or NF99HF available from Alfa Laval, which has a functional layer of polyamide, a nano-filtration membrane NF-45, NF-90, NF-200, or NF400 available from Filmtech corporation, which has a functional layer of crosslinked piperazine polyamide, and a nano-filtration membrane module SU-210, SU-220, SU-600, or SU-610 available from TORAY INDUSTRIES, INC., including UTC60 available from TORAY INDUSTRIES, INC., which has a functional layer that contains crosslinked piperazine polyamide as a main component and a polyamide containing a component represented by Formula (1) are preferable. A nano-filtration membrane module SU-210, SU-220, SU-600, or SU-610 available from TORAY INDUSTRIES, INC., including UTC60 available from TORAY INDUSTRIES, INC., which has a functional layer that contains crosslinked piperazine polyamide as a main component and a polyamide containing a component represented by Formula (1) is more preferable.

The pH of ammonia-treated sugar solution to pass through the nano-filtration membrane is not particularly limited, and the pH is preferably 1 to 5. When the pH is less than 1, the membrane is denatured by use for an extended period of time, and membrane performances such as flux and permeability ratio significantly decrease. When the pH is more than 5, the removal ratio of fermentation inhibitor may significantly decrease. When the pH of the ammonia-treated sugar solution is adjusted within the range and the ammonia-treated sugar solution is subjected to filtration through the nano-filtration membrane, the removal ratio of the fermentation inhibitor can be improved. When the pH of the ammonia-treated sugar solution falls within the range, there is an effect of suppressing fouling of the nano-filtration membrane. Therefore, the nano-filtration membrane can be used stably for an extended period of time.

Acid or alkali used in the adjustment of pH of the ammonia-treated sugar solution is not particularly limited. Examples of the acid may include hydrochloric acid, sulfuric acid, nitric acid, and phosphoric acid. Sulfuric acid, nitric acid, and phosphoric acid are preferable from the viewpoint of difficulty of inhibition during fermentation, and sulfuric acid is more preferable from the viewpoint of economy. It is preferable that the alkali be ammonia, sodium hydroxide, calcium hydroxide, or an aqueous solution containing any of them from the viewpoint of economy, more preferably ammonia or sodium hydroxide, which is a monovalent ion, from the viewpoint of membrane fouling, and further preferably ammonia from the viewpoint of difficulty of inhibition during fermentation.

A step of adjusting the pH of the ammonia-treated sugar solution may be performed at any time as long as the step is performed before the ammonia-treated sugar solution is caused to pass through the nano-filtration membrane. When an enzyme is used for hydrolysis of cellulosic biomass, the pH may be adjusted to 5 or lower during a hydrolysis reaction. When the pH is decreased to 4 or lower in a process of recycling an enzyme contained in a filtrate, deactivation of the enzyme is likely to occur. Therefore, it is preferable that the pH be adjusted after removal of the enzyme contained in the filtrate.

The temperature of the ammonia-treated sugar solution that is caused to pass through the nano-filtration membrane is not particularly limited. The temperature may be appropriately set from the viewpoint of increasing the removal performance of the fermentation inhibitor during filtration through the used nano-filtration membrane. Specifically, when the nano-filtration membrane is used for filtration, it is preferable that the temperature of the ammonia-treated sugar solution be 40° C. to 80° C. This is because the removal performance of the fermentation inhibitor by the nano-filtration membrane is enhanced. When the temperature of the ammonia-treated sugar solution during filtration through the nano-filtration membrane is 40° C. or higher, the removal performance of the fermentation inhibitor in the ammonia-treated sugar solution increases. When the temperature of the ammonia-treated sugar solution is higher than 80° C., the nano-filtration membrane is denatured. Therefore, the membrane properties may be lost. Accordingly, when the temperature of the ammonia-treated sugar solution falls within the above-mentioned range, the removal performance of the fermentation inhibitor through the nano-filtration membrane can be improved.

Specifically, a method using nano-filtration can be performed in accordance with a method described in WO No. 2010/067785.

When the ammonia-treated sugar solution is subjected to filtration through the nano-filtration membrane, the fermentation inhibitor can be removed more effectively by addition of water to the ammonia-treated sugar solution. By the amount of water to be added, the content of the fermentation inhibitor contained in the purified sugar solution after nano-filtration can be adjusted. Specifically, as the amount of water to be added is larger, the content of the fermentation inhibitor contained in the purified sugar solution after nano-filtration decreases.

Coumaramide and/or ferulamide in the ammonia-treated sugar solution are thus removed by purification, to obtain a purified sugar solution having a predetermined concentration.

As described above, according to the method of producing a sugar solution according to this example, coumaramide and/or ferulamide in the ammonia-treated sugar solution that is obtained by enzymatic saccharification of the ammonia-treated product obtained by treating the cellulosic biomass with the treatment agent containing ammonia are removed by purification. Thus, a purified sugar solution having a predetermined concentration can be obtained. When specific coumaramide and/or ferulamide contained in the ammonia-treated sugar solution as fermentation inhibitors are decreased in advance before fermentation of the sugar solution, the fermentation efficiency can be improved.

By fermentation of the resultant purified sugar solution used as a fermentation raw material, ethanol can be produced. A method of producing ethanol from the purified sugar solution obtained by the method of producing a sugar solution according to this example is not particularly limited. Examples of the method of producing ethanol may include a two-stage fermentation process described in Japanese Patent Application Laid-Open No. 2009-296983. In the two-step fermentation process, a hexose such as glucose and mannose is converted by yeast or bacteria in a primary fermentation step into ethanol, and a pentose such as xylose is then converted in a secondary fermentation step into ethanol. As fungi used in the primary fermentation step, known germs can be used. Among the fungi, yeast such as *Saccharomyces cerevisiae* is preferable. This is because the yeast has high resistance to ethanol and enables ethanol having a concentration of 5% or more to be produced. As fungi used in the secondary fermentation step, a pentose assimilation yeast such as *Pichia stipitis* can be used, and in particular, a strain that is provided with a performance resistant to fermentation inhibition is preferable.

In the purified sugar solution obtained by the method of producing a sugar solution according to this example, specific coumaramide and/or ferulamide contained as the fermentation inhibitors in the ammonia-treated sugar solution that is obtained by treating cellulosic biomass with the treatment agent containing ammonia are removed. Therefore, when the purified sugar solution is used as a fermentation raw material, fermentation is not inhibited. Accordingly, use of the purified sugar solution obtained by the method of producing a sugar solution according to this example as a fermentation raw material can improve the efficiency of production of ethanol.

EXAMPLES

Hereinafter, the content of this disclosure will be described in detail with reference to Examples and Comparative Examples, but this disclosure is not limited to the following Examples.

Example 1: Preparation and Analysis of Purified Sugar Solution

A. Preparation of Ammonia-Treated Sugar Solution
1. Crushing Treatment of Cellulosic Biomass Erianthus was used as cellulosic biomass. The erianthus was crushed with a cutter mill while the particle size was controlled with a screen having a 4-mm opening. An average particle diameter (d50) measured by a laser diffraction method was about 975 μm. The crushed erianthus was dried at a temperature of 40° C. under a reduced pressure of 5 kPa all day and night. The moisture content of the dried erianthus was about 0.5% by mass based on the mass of the dried erianthus.

2. Treatment of Cellulosic Biomass with Ammonia

The crushed and dried cellulose as cellulose chips was treated with ammonia. A stainless steel autoclave equipped with a stirrer having a capacity of about 5 L was charged with 200 g of the cellulose chips. Subsequently, introduction of pressurized nitrogen gas into the autoclave and depressurization were repeated to remove air from the autoclave and replace air by nitrogen gas. The autoclave was then heated to 120° C. After heating, the autoclave was depressurized, and nitrogen gas was evacuated under reduced pressure. On the other hand, pressurized ammonia was introduced into another pressure vessel, and heated to a temperature of slightly higher than 120° C. Then, a valve provided in a piping connecting the autoclave and the pressure vessel was opened to introduce ammonia into the autoclave so that the pressure at a temperature of 120° C. was 1.2 MPa. The cellulose chips were treated with ammonia under the temperature and pressure conditions for 2.5 hours with stirring. Subsequently, the autoclave was depressurized and ammonia was evacuated. Further, nitrogen gas was caused to pass through the autoclave to remove residual ammonia in cellulose chip particles. Thus, pretreated biomass was obtained. This biomass was used as ammonia-treated cellulose (ammonia-treated product).

3. Hydrolysis of Ammonia-Treated Cellulose 7.6 kg of water was added to 0.4 kg of ammonia-treated cellulose so that the concentration of the ammonia-treated cellulose was 5%. To the resultant, a small amount of concentrated sulfuric acid or aqueous sodium hydroxide was added to adjust the pH to 5. Subsequently, a cellulase preparation derived from *Trichoderma reesei* (Accellerase DUET, available from Genencor, Inc.) was added in an amount of 1/100 of the amount of dried ammonia-treated cellulose in terms of the amount of enzyme protein. A saccharification reaction was performed at 50° C. for 24 hours. The substance obtained by the saccharification reaction was used as a hydrolysate.

4. Solid-Liquid Separation of Hydrolysate

The resultant hydrolysate was centrifuged and separated into a solution component as well as an undecomposed cellulose and lignin. The solution component was subjected to filtration through a micro-filtration membrane having a micropore diameter of 0.45 μm (Stericup, available from Millipore Corporation) to remove micron-scale insoluble particles. The solution component obtained by the method described above was used as an ammonia-treated sugar solution.

B. Preparation of Purified Sugar Solution
5. Condensation of Sugar Through Nano-Filtration Membrane The resulting ammonia-treated sugar solution was subjected to filtration through a nano-filtration membrane (UTC-60, available from TORAY INDUSTRIES, INC.) at normal temperature and an operation pressure of 4 MPa. The concentrated solution obtained by the filtration was used as a purified sugar solution. As a membrane separation device, a flat membrane unit (SEPA CF-II, available from GE Osmonics, effective membrane area: 140 cm$^2$) was used.

C. Analysis of Ammonia-Treated Sugar Solution

Saccharides, organic acid, and an aromatic compound in the ammonia-treated sugar solution obtained in "4. Solid-Liquid Separation of Hydrolysate" were analyzed. Each analysis condition of the saccharides, organic acid, and aromatic compound in the ammonia-treated sugar solution is shown below.

HPLC Analysis Condition
1. Analysis Condition of Saccharides

The concentrations of glucose and xylose in the ammonia-treated sugar solution were determined under high performance liquid chromatography (HPLC) conditions shown below by comparison to a standard sample:
Apparatus: ACQUITY UPLC System (manufactured by Waters)
Column: ACQUITY UPLC BEH Amide 1.7 μm 2.1×100 mm Column (manufactured by Waters)
Mobile phase: A liquid; 80% acetonitrile+0.2% TEA, B liquid; 30% acetonitrile+0.2% TEA
Flow rate: 0.3 mL/min
Temperature: 55° C.

2. Analysis Condition of Organic Acid

The concentration of acetic acid in the ammonia-treated sugar solution was determined under HPLC conditions shown below by comparison to the standard sample:
Apparatus: Hitachi High-Performance Liquid Chromatograph Lachrom elite (manufactured by Hitachi)
Column: GL-C610H-S (manufactured by Hitachi)
Mobile phase: 3 mM perchloric acid
Reaction liquid: bromothymol blue solution Detection method: UV-VIS detector
Flow rate mobile phase: 0.5 mL/min, reaction liquid: 0.6 mL/min
Temperature: 60° C.
3. Analysis Condition of Aromatic Compound The concentrations of coumaric acid, coumaramide, and ferulamide in the ammonia-treated sugar solution were determined under HPLC conditions shown below by comparison to the standard sample. At this time, the UV absorption spectrum (measurement wavelength: 200 nm to 400 nm) of each detection peak was obtained.
Apparatus: Hitachi High-Performance Liquid Chromatograph Lachrom elite (manufactured by Hitachi)
Column: Synergi 2.5 μm Hydro-RP 100A (manufactured by Phenomenex)
Detection method: Diode Array detector
Flow rate: 0.6 mL/min
Temperature: 40° C.

Figure 2:
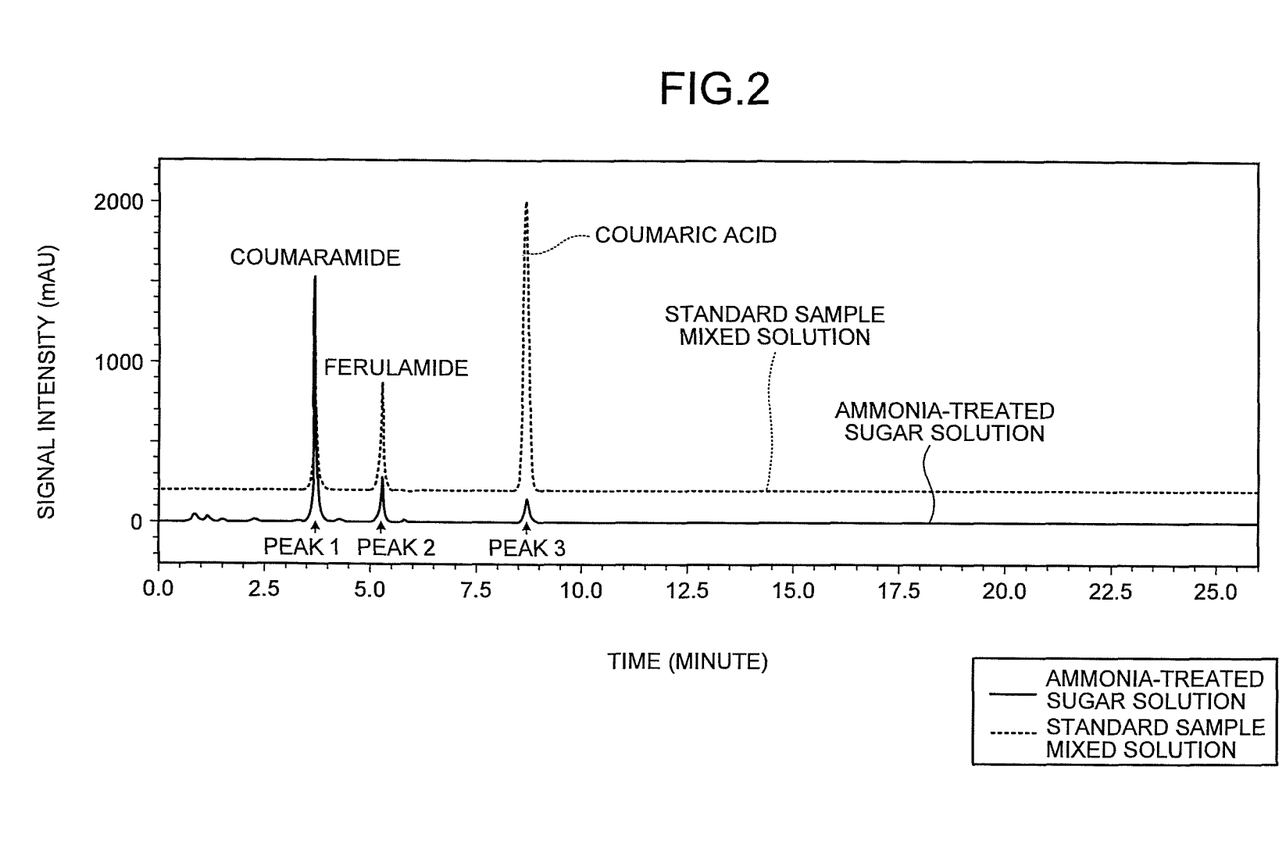
FIG. 2 is a diagram showing results of analysis of aromatic compounds in an ammonia-treated sugar solution by HPLC.

The saccharides in the resulting ammonia-treated sugar solution were analyzed under the HPLC conditions described in "1. Analysis Condition of Saccharides." As confirmed from the result, glucose and xylose are contained as main saccharide components. The organic acid in the ammonia-treated sugar solution was analyzed under the HPLC conditions described in "2. Analysis Condition of Organic Acid." As seen from the result, acetic acid was contained as a main organic acid component. The aromatic compound in the ammonia-treated sugar solution was analyzed under the HPLC conditions described in "3. Analysis Condition of Aromatic Compound." The result is shown in FIG. 2. As seen in FIG. 2, three main peaks (see Peaks 1, 2, and 3) were detected from the ammonia-treated sugar solution.

Among these, the peak 3 was found to be a peak of coumaric acid since the HPLC elution times of the peak 3 and the coumaric acid standard sample coincided with each other. The elution times of two remaining compounds (peaks 1 and 2) did not coincide with those of all standard samples of HMF, furfural, vanillin, acetovanillone, ferulic acid, coniferyl aldehyde, and guaiacol, which are known as an aromatic compound contained in a sugar solution derived from cellulosic biomass. The two peaks (peaks 1 and 2) were isolated by HPLC, and the molecular weights thereof were analyzed by LC/MS (LCMS-IT-TOF and LC20A, manufactured by Shimadzu Corp.).

As shown from the results, the molecular weights of the peaks 1 and 2 were 163.063 and 193.074, respectively. It is assumed that coumaric acid and ferulic acid are subjected to a condensation reaction with ammonia molecules, to produce coumaramide and ferulamide, respectively. The molecular weights calculated from the structural formulae of coumaramide and ferulamide were 163.172 and 193.198, respectively, and corresponded to the molecular weights obtained by LC/MS, respectively. Therefore, it is believed that the two remaining peaks (peaks 1 and 2) in the ammonia-treated cellulose sugar solution are coumaramide and ferulamide.

Coumaramide and ferulamide standard samples were prepared by custom synthesis (contractor: VSN, Inc., synthesis laboratory), and the HPLC elution times of the synthesized standard samples were measured. As a result, the elution times (3.74 min) of the peak 1 in the ammonia-treated sugar solution and the coumaramide standard sample in a mixed solution of the standard samples completely coincided with each other, and the elution times (5.25 min) of the peak 2 in the ammonia-treated sugar solution and the ferulamide standard sample in a mixed solution of the standard samples completely coincided with each other (see FIG. 2).

Figure 3:
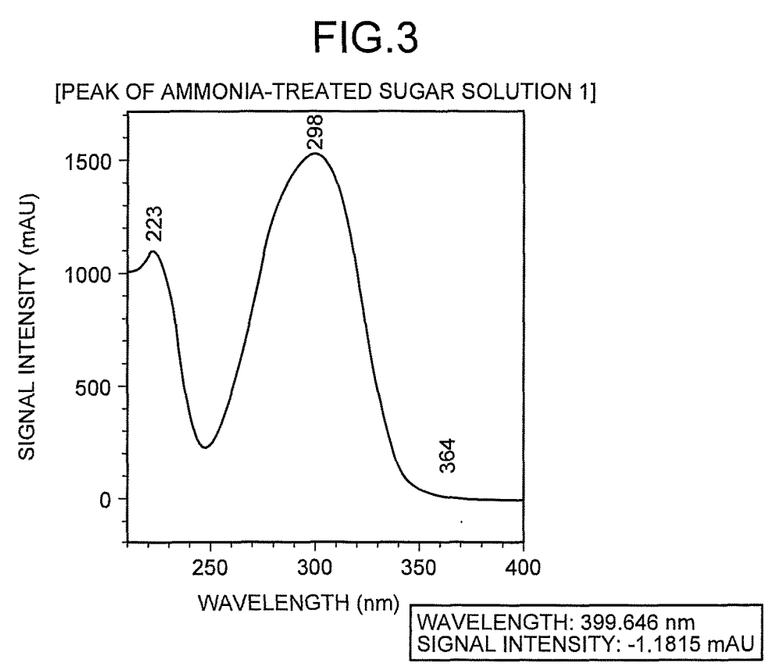
FIG. 3 is a diagram showing a UV absorption spectrum of peak 1 of the ammonia-treated sugar solution.
Figure 4:
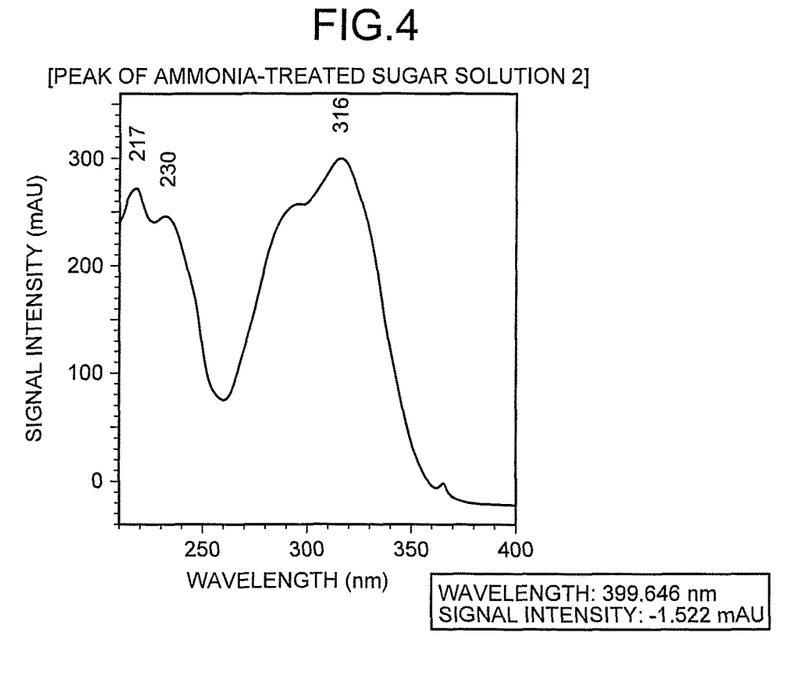
FIG. 4 is a diagram showing a UV absorption spectrum of peak 2 of the ammonia-treated sugar solution.
Figure 5:
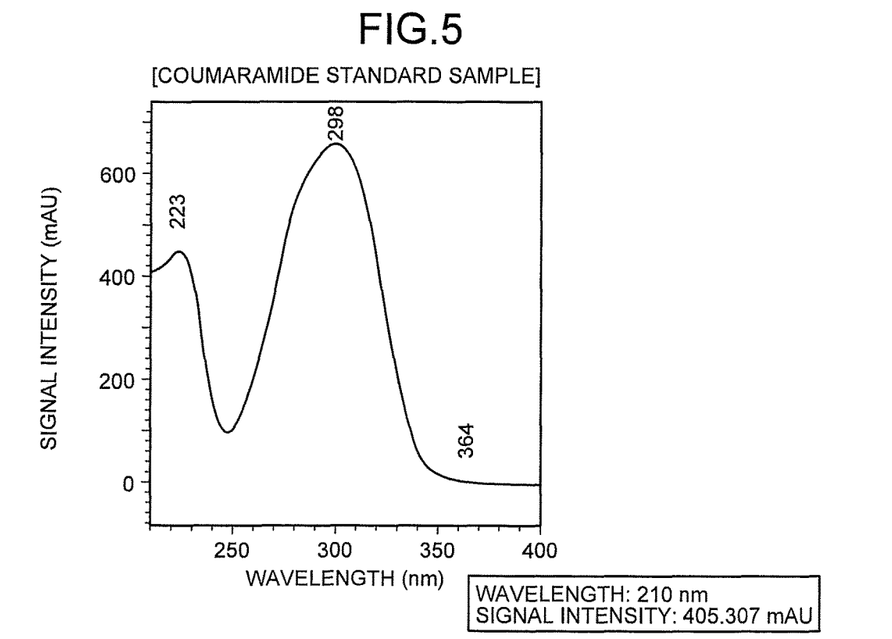
FIG. 5 is a diagram showing a UV absorption spectrum of a coumaramide standard sample.
Figure 6:
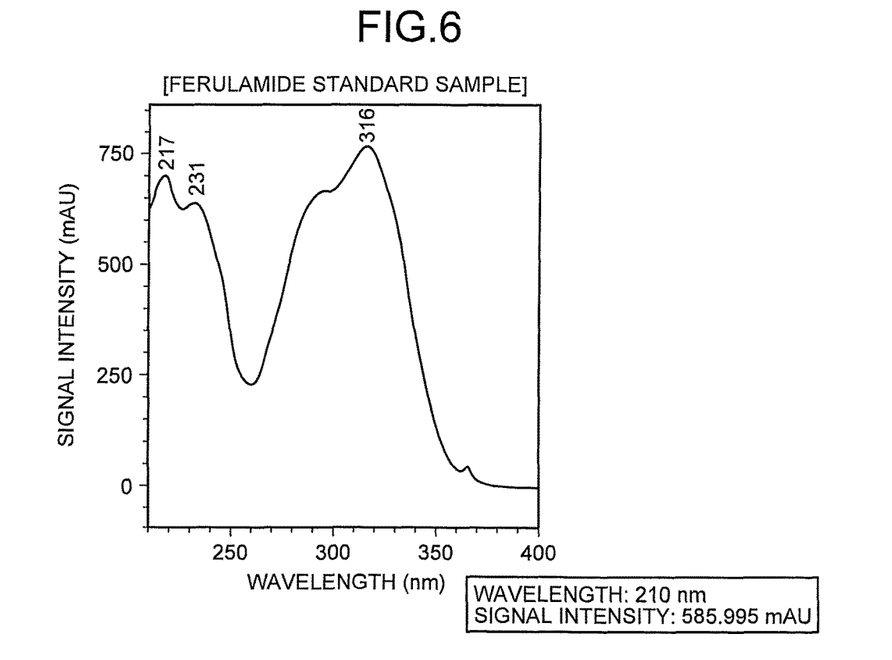
FIG. 6 is a diagram showing a UV absorption spectrum of a ferulamide standard sample.

FIGS. 3 to 6 show each UV absorption spectrum of the peaks 1 and 2 in the ammonia-treated sugar solution, the coumaramide standard sample, and the ferulamide standard sample, which were obtained in HPLC. Herein, the measurement wavelength is 200 nm to 400 nm. As shown in FIGS. 3 and 5, the UV absorption spectra of the peak 1 in the ammonia-treated sugar solution and the coumaramide standard sample coincided with each other. As shown in FIGS. 4 and 6, the UV absorption spectra of the peak 2 in the ammonia-treated sugar solution and the ferulamide standard sample coincided with each other.

As can be seen from the analysis results, the peaks 1 and 2 in the ammonia-treated sugar solution that is a hydrolysate of ammonia-treated cellulose are coumaramide and ferulamide, respectively, and the ammonia-treated sugar solution contained a large amount of the compounds.

D. Analysis of Purified Sugar Solution

Table 1 shows each component concentration in the raw material solution (ammonia-treated sugar solution) before filtration, the concentrated sugar solution (purified sugar solution) after filtration, and a permeation solution. The analysis of the components was performed in accordance with the HPLC analysis conditions described in "C. Analysis of Ammonia-Treated Sugar solution."

TABLE 1

|  | Glucose (g/L) | Xylose (g/L) | Acetic Acid (g/L) | Coumaric Acid (g/L) | Coumaramide (g/L) | Ferulamide (g/L) |
| --- | --- | --- | --- | --- | --- | --- |
| Raw Material Solution | 17.0 | 11.0 | 0.157 | 0.037 | 0.491 | 0.189 |
| Concentrated Sugar Solution | 99.6 | 53.9 | 0.151 | 0.079 | 0.622 | 0.454 |
| Permeation Solution | 1.16 | 1.4 | 0.169 | 0.030 | 0.317 | 0.064 |

As is clear from Table 1, when the ammonia-treated sugar solution was subjected to filtration through the nano-filtration membrane, the saccharide components, that is, glucose and xylose, in the concentrated sugar solution were concentrated 5.9 times and 4.9 times, respectively. On the other hand, the components other than saccharide (acetic acid, coumaric acid, coumaramide, and ferulamide) were concentrated about 1 to about 2.4 times. When the ammonia-treated sugar solution was subjected to filtration through the nano-filtration membrane, most of the saccharide components in the raw material solution and most of the components other than saccharide could be effectively separated into a non-permeation side and a permeation side, respectively.

Comparative Example 1: Consideration of Case where Saccharide is Concentrated from Ammonia-Treated Sugar Solution Using Reverse Osmosis Membrane Filtration was performed in the same manner as in "5. Condensation of Saccharide through Nano-Filtration Membrane" in Example 1 except that a reverse osmosis membrane (UTC-80, available from TORAY INDUSTRIES, INC.) was used as a separation membrane and the operation pressure was 5 MPa. Table 2 shows each component concentration in the raw material solution (ammonia-treated sugar solution) before filtration, the concentrated sugar solution (purified sugar solution) after filtration, and a permeation solution. Note that the components were analyzed by HPLC in the same manner as described above.

TABLE 2

|  | Glucose (g/L) | Xylose (g/L) | Acetic Acid (g/L) | Coumaric Acid (g/L) | Coumaramide (g/L) | Ferulamide (g/L) |
| --- | --- | --- | --- | --- | --- | --- |
| Raw Material Solution | 17.0 | 11.0 | 0.157 | 0.037 | 0.491 | 0.189 |
| Concentrated Sugar Solution | 102.9 | 59.5 | 0.743 | 0.160 | 2.050 | 2.053 |
| Permeation Solution | 0.2 | 0.1 | 0 | 0 | 0 | 0 |

As is clear from Table 2, monosaccharide components including glucose and xylose and other components were hardly contained in the permeation solution. It is confirmed that when the reverse osmosis membrane is used as a separation membrane, the saccharide components and coumaramide and ferulamide in the ammonia-treated sugar solution cannot be separated.

Example 2: Growth Test Using Model Solution Containing Coumaramide, Coumaric Acid, and Ferulamide In main culture of "A. Growth Test of *Pichia Stipitis* using Model Sugar solution" described below, any one of coumaramide, coumaric acid, and ferulamide was added in a concentration of 2 ppm to 200 ppm as an additive in a medium, and the medium was subjected to a growth test. As a positive control, a YPDX medium free of an additive was subjected to the same test.

A. Growth Test of *Pichia Stipitis* Using Model Sugar Solution

A *Pichia stipitis* NBRC1687 strain was statically cultured at 25° C. in a YPDX agar medium produced by adding 2% agar to a YPDX medium shown in Table 3 below (preprecu­lture). One of colonies formed on the agar medium was inoculated into 10 mL of the YPDX medium with a platinum loop, and cultured at 25° C. and 120 spm in a test tube with a volume of 20 mL for 48 hours under shaking (preculture). One mL of medium after the preculture was added to 9 mL of YPDX medium, and culture was further continued at 25° C. and 60 spm in a test tube with a volume of 20 mL (main culture). 0, 24, and 48 hours after initiation of the culture, sampling was performed, the monosaccharide concentration and the absorbance (OD660) were measured. Thus, growth of fungus bodies was observed.

TABLE 3

| Composition | Composition Concentration (g/L) |
| --- | --- |
| Glucose | 10 |
| Xylose | 10 |
| Polypeptone | 20 |
| Yeast Extrast | 10 |

Table 4 shows analysis results of concentrations of glucose and xylose in the medium during sampling in this Example.

TABLE 4

| | PC | Coumaramide (ppm) | | | Coumaric Acid (ppm) | | | Ferulamide (ppm) | | |
| --- | --- | --- | --- | --- | --- | --- | --- | --- | --- | --- |
| | 0 | 2 | 20 | 200 | 2 | 20 | 200 | 2 | 20 | 200 |
| Glucose | | | | | | | | | | |
| 0 h | 10 | 10 | 10 | 10 | 10 | 10 | 10 | 10 | 10 | 10 |
| 24 h | 2.4 | 2.3 | 4.82 | 5.9 | 2.6 | 2.6 | 3.6 | 2.3 | 6.6 | 6.7 |
| 48 h | 0 | 0 | 0 | 0 | 0 | 0 | 0 | 0 | 0 | 0 |
| Xylose | | | | | | | | | | |
| 0 | 10 | 10 | 10 | 10 | 10 | 10 | 10 | 10 | 10 | 10 |
| 24 h | 2.4 | 2.3 | 9.7 | 9.5 | 2.6 | 8.7 | 9.2 | 2.3 | 9.3 | 9.7 |
| 48 h | 0 | 0 | 0 | 0.4 | 0 | 0 | 0 | 0 | 0 | 5.2 |

As is clear from Table 4, when the concentrations of the additives were 20 ppm or more, consumption of xylose was delayed in all the additives as compared with the positive control, and growth inhibition occurred. On the other hand, when the concentrations of the additives were 2 ppm, growth inhibition was not observed at all in all the additives. Coumaramide and ferulamide were superior to coumaric acid in growth inhibitory, this trend was found to be particularly remarked in a consumption rate of glucose. Specifically, it was found that coumaramide and ferulamide were fermentation inhibitors in the culture of *Pichia stipitis*.

Example 3: Growth Test of Concentrated Sugar Solution Through Nano-Filtration Membrane A concentrated sugar solution of ammonia-treated sugar solution through the nano-filtration membrane (hereinafter referred to as NF concentrated solution 1) was adjusted by the method described in "5. Condensation of Saccharide through Nano-Filtration Membrane" in Example 1. In the NF concentrated solution 1, water was mixed in an amount the same as the amount of the NF concentrated solution 1, and filtration through the nano-filtration membrane was performed again under conditions described in "5. Condensation of Saccharide through Nano-Filtration Membrane" in Example 1 to obtain an NF concentrated solution 2. To the NF concentrated solution 2, water was added in an amount the same as the amount of the NF concentrated solution 2, and filtration through the nano-filtration membrane was performed again under conditions described in "5. Condensation of Saccharide through Nano-Filtration Membrane" in Example 1 to obtain an NF concentrated solution 3. Table 5 shows each component concentration of the NF concentrated solutions 1 to 3 and the concentrated sugar solution obtained through a reverse osmosis membrane (hereinafter RO concentrated solution) by the method described in Comparative Example 1.

A growth test was performed using each sugar solution by a method described in "B. Growth Test of *Pichia Stipitis* using Concentrated solution of Ammonia-Treated Sugar solution" described below. Test results are shown in Table 5. In the results in the growth test, cases where the absorbance (OD660) 48 hours after initiation of the culture is 50% to 100%, 10% to 50%, and less than 10%, relative to the positive control are represented by ++, +, and −, respectively. The absorbance (OD660) of the positive control after 48 hours was about 15.

B. Growth Test of *Pichia Stipitis* Using Concentrated Solution of Ammonia-Treated Sugar Solution In a growth test using the concentrated solution of the ammonia-treated sugar solution, culture was performed in the same manner as in "A. Growth Test of *Pichia Stipitis* using Model Sugar solution" except that a medium in which polypeptone and an yeast extract were added to the concentrated solution of the ammonia-treated sugar solution so that the concentrations thereof were the same as those in the YPDX medium described in Table 3 was used as the medium for a main culture. The positive control was cultured in the same manner as in "A. Growth Test of *Pichia Stipitis* using Model Sugar solution."

with reverse osmosis membrane. As can be seen from the results and Example 2, when purification was performed in the nano-filtration so that the total concentration of coumaramide and ferulamide was 1,100 ppm or less, effective growth of a microorganism was possible.

Example 4: Ethanol Production Test Using Ammonia-Treated Sugar Solution

Ethanol was produced using the concentrated sugar solution (NF concentrated solution) obtained from the ammonia-treated sugar solution through the nano-filtration membrane and the concentrated sugar solution (RO concentrated solution) obtained using the reverse osmosis membrane by the method described in Comparative Example 1 in accordance with "C. Ethanol Production Test of *Pichia Stipitis* using Ammonia-Treated Sugar solution" described below. The fermentation properties thereof were compared with each other.

C. Ethanol Production Test of *Pichia Stipitis* Using Ammonia-Treated Sugar Solution The ethanol production test from the ammonia-treated sugar solution was performed in accordance with a two-step fermentation process described in Japanese Patent Application Laid-Open No. 2009-296983. *Saccharomyces cerevisiae* was cultured using an ammonia-treated sugar solution concentrated solution to convert glucose into ethanol as primary fermentation. In this case, it was confirmed that even when any of the NF concentrated solution and the RO concentrated solution was used, fermentation was not inhibited.

Figure 7:
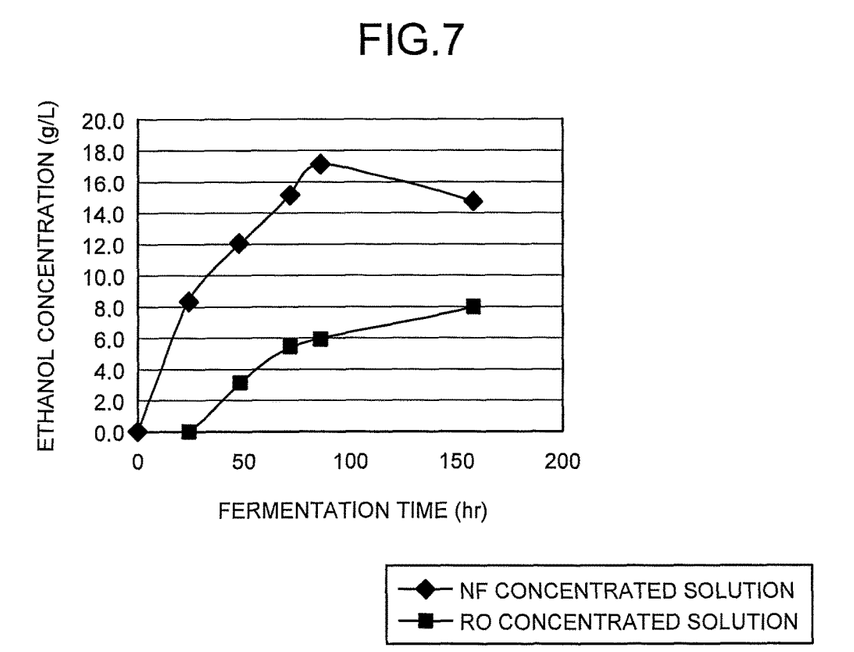
FIG. 7 is a diagram showing the relationship between a fermentation time and an ethanol concentration of an NF concentrated solution and an RO concentrated solution.

Subsequently, *Pichia stipitis* was cultured using a primary fermentation solution of which the ethanol concentration was adjusted to 10 g/L with a rotary evaporator to convert xylose in the primary fermentation solution into ethanol as secondary fermentation. In the secondary fermentation, the relationship between the fermentation time and the ethanol concentration of the NF concentrated solution-derived primary fermentation solution and the RO concentrated solution-derived primary fermentation solution is shown in FIG. 7, and the relationship between the fermentation time and

TABLE 5

| | Glucose (g/L) | Xylose (g/L) | Coumaric Acid (g/L) | Coumaramide (g/L) | Ferulamide (g/L) | (a) + (b) (ppm) | Growth of Microorganism |
|---|---|---|---|---|---|---|---|
| NF Concentrated Solution 1 | 99.6 | 53.9 | 0.079 | 0.622 | 0.454 | 1076 | + |
| NF Concentrated Solution 2 | 98.3 | 51.5 | 0.053 | 0.436 | 0.345 | 781 | + |
| NF Concentrated Solution 3 | 97.7 | 50.2 | 0.032 | 0.213 | 0.217 | 430 | ++ |
| RO Concentrated Solution (Comparative Example) | 102.9 | 59.5 | 0.160 | 2.050 | 0.809 | 2859 | − |

Figure 8:
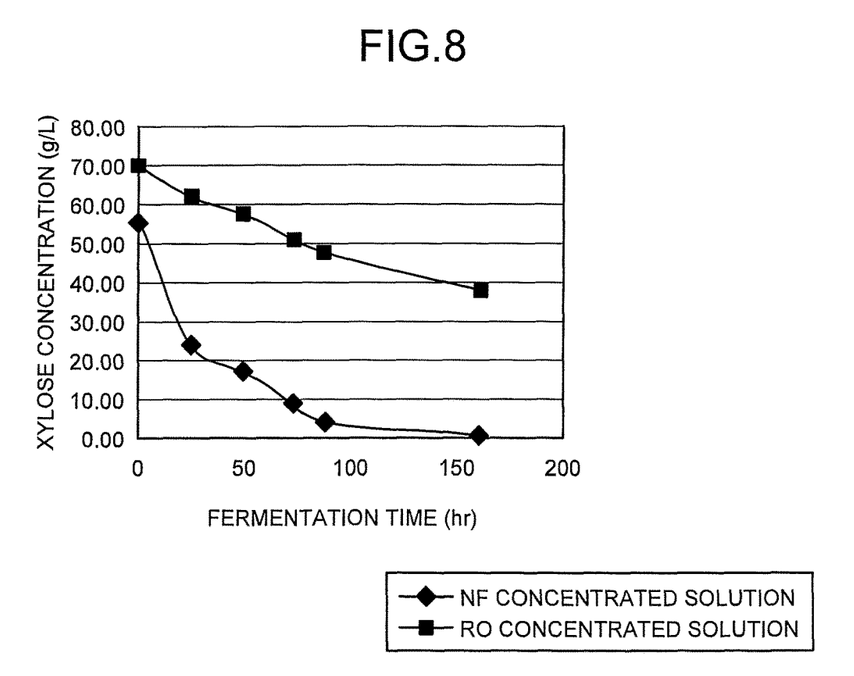
FIG. 8 is a diagram showing the relationship between a fermentation time and a xylose concentration of the NF concentrated solution and the RO concentrated solution.

As is clear from Table 5, at each time when addition of water to the NF concentrated solution and nano-filtration were repeated, the concentrations of coumaric acid, coumaramide, and ferulamide decreased. On the other hand, when filtration through the reverse osmosis membrane was performed, these substances were markedly concentrated. From the results of the growth test, when the total concentration of coumaramide and ferulamide in the sugar solution is 1,100 ppm or less, growth is possible. From the results, it was confirmed that removal of coumarmide and ferulamide required treatment with nano-filtration membrane but not the xylose concentration of the NF concentrated solution-derived primary fermentation solution and the RO concentrated solution-derived primary fermentation solution is shown in FIG. 8. As shown in FIGS. 7 and 8, ethanol production by the RO concentrated solution-derived primary fermentation solution was largely inhibited in the secondary fermentation by *Pichia stipitis*. The consumption rate of xylose, the ethanol production rate, and the ethanol final production concentration decreased as compared with ethanol production by the NF concentrated solution-derived primary fermentation solution. Therefore, it was apparent that an alcohol fermentation inhibitor was markedly concentrated by concentration through the reverse osmosis membrane as compared with concentration through the nano-filtration membrane.

Example 5: Verification of Ethanol Production Inhibition by Permeation Solution after Membrane Filtration Ethanol was produced using a filtrate (permeation solution) obtained during production of the NF concentrated solution and RO concentrated solution. The permeation solutions derived from the NF concentrated solution and the RO concentrated solution are referred to as NF permeation solution and RO permeation solution, respectively. Each permeation solution was concentrated 3 times with a rotary evaporator. A yeast extract, polypeptone, and xylose were added to the concentrated permeation solution so that the final concentrations were 0.5%, 1.0%, and 7.0%, respectively. To the prepared liquid medium, Pichia stipitis was added, to produce ethanol. As a control, a liquid medium in which a yeast extract, polypeptone, and xylose were added to water so that the composition was the same as described above was used, and the same verification was performed.

Figure 9:
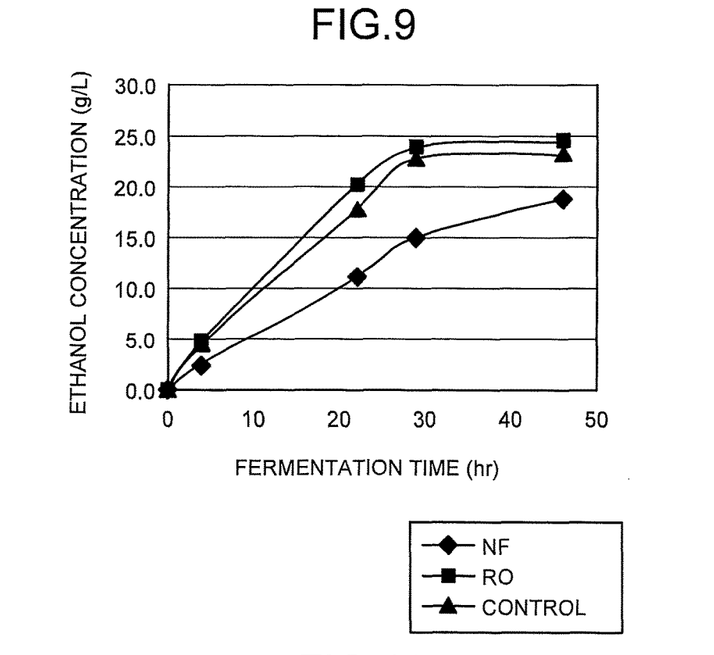
FIG. 9 is a diagram showing the relationship between the fermentation time and the ethanol concentration of the NF concentrated solution and the RO concentrated solution.
Figure 10:
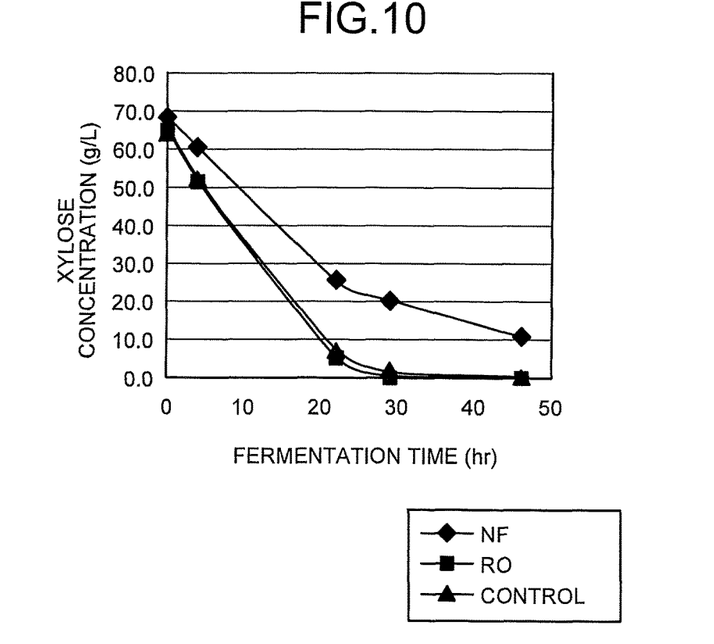
FIG. 10 is a diagram showing the relationship between the fermentation time and the xylose concentration of the NF concentrated solution and the RO concentrated solution.

FIG. 9 shows the relationship between the fermentation time and the ethanol concentration of the NF concentrated solution and the RO concentrated solution. FIG. 10 shows the relationship between the fermentation time and the xylose concentration of the NF concentrated solution and the RO concentrated solution. As shown in FIGS. 9 and 10, xylose consumption and ethanol production that were the same as those in the control were performed in a medium containing the RO permeation solution. In a medium containing the NF permeation solution, the xylose consumption rate decreased to about 75% of that of the control, and the ethanol production rate decreased to about 60%. As is apparent from the results, an ethanol-producing inhibitor permeated into the nano-filtration membrane in a concentration treatment of the ammonia-treated sugar solution through the nano-filtration membrane and were accumulated in the filtrate. Therefore, the ethanol-producing inhibitor can be removed by the concentration treatment through the nano-filtration membrane.

Example 6: Ammonia-Treated Cellulose Concentration During Saccharification

Water was added to 0.4 kg of ammonia-treated cellulose described in "2. Treatment of Cellulosic Biomass with Ammonia" of Example 1 according to the amount to be added during preparation described in Table 6 to adjust the concentration of ammonia-treated cellulose to 5, 10, 15, and 20%. To the resultant, a small amount of concentrated sulfuric acid was added to adjust the pH to 5, and a cellulase preparation (Accellerase DUET, available from Genencor) was then added in an amount of 1/100 of the amount of dried ammonia-treated cellulose in terms of the amount of enzyme protein. An enzymatic saccharification reaction was performed at 50° C. for 24 hours. The resultant hydrolysate was centrifuged and separated into a solution component as well as a undecomposed cellulose or lignin. The solution component was subjected to filtration through a micro-filtration membrane having a micropore diameter of 0.45 μm (Stericup, available from Millipore Corporation) to remove micron-scale insoluble particles. The solution component obtained by the method was subjected to a nano-filtration membrane treatment in accordance with "5. Condensation of Saccharide through Nano-Filtration Membrane" of Example 1, to obtain an NF concentrated solution. The concentration ratio was adjusted so that the glucose concentration in the concentrated solution was about 10%. Each component concentration in the concentrated solution is shown in Table 7.

TABLE 6

| Ammonia-treated Cellulose Concentration (% by mass) During Enzymatic Saccharification | Amount of Added Water During Preparation (kg) |
|---|---|
| 5 | 7.6 |
| 10 | 3.6 |
| 15 | 2.6 |
| 20 | 1.6 |

TABLE 7

| Ammonia-treated Cellulose Concentration (% by mass) During Enzymatic Saccharification | Concentration in NF Concentrated Solution (g/L) | | | | |
|---|---|---|---|---|---|
| | Glucose | Xylose | Coumaramide (a) | Ferulamide (b) | (a) + (b) (ppm) |
| 5 | 99.6 | 53.9 | 0.62 | 0.45 | 1070 |
| 10 | 101.2 | 53.4 | 0.61 | 0.47 | 1080 |
| 15 | 100.4 | 52.2 | 0.72 | 0.53 | 1250 |
| 20 | 102.3 | 52.8 | 0.80 | 0.59 | 1390 |

As is clear from Table 7, when the ammonia-treated cellulose concentration during enzymatic saccharification was 5% and 10%, the total concentration of coumaramide and ferulamide in the NF concentrated solution was 1,100 ppm or less. When the ammonia-treated cellulose concentration during enzymatic saccharification was 15% and 20%, the total concentrations of coumaramide and ferulamide markedly increased, and were 1,250 ppm and 1,390 ppm, respectively. As can be seen from the results and Example 5, when the total concentration of coumaramide and ferulamide in the sugar solution is 1,100 ppm or less, a microorganism is viable, and ethanol can be efficiently produced by the microorganism. Therefore, it is preferable that the concentration of ammonia-treated cellulose during enzymatic saccharification be 10% or less.

The invention claimed is:

1. A method of producing a sugar solution comprising:
   a pretreatment step of treating cellulosic biomass with a treatment agent containing ammonia to obtain an ammonia-treated product;
   an ammonia-treated sugar solution preparation step of enzymatically saccharifying the ammonia-treated product to obtain an ammonia-treated sugar solution;
   a purification treatment step of adding water to the ammonia-treated sugar solution while treating the ammonia-treated sugar solution with a nano-filtration membrane; and
   a purified sugar solution preparation step of removing coumaramide and/or ferulamide in the ammonia-treated sugar solution by purification to obtain a purified sugar solution;
   wherein a concentration of coumaramide and/or ferulamide in the purified sugar solution is 10 to 1,100 ppm.

2. The method according to claim 1, wherein the cellulosic biomass contains herbaceous biomass.

3. The method according to claim 1, wherein the ammonia-treated sugar solution contains enzymatically saccharified ammonia-treated product in a concentration of 1 to 10% by mass.

* * * * *